US010697928B2

(12) United States Patent
Chey et al.

(10) Patent No.: US 10,697,928 B2
(45) Date of Patent: Jun. 30, 2020

(54) RECONFIGURABLE GAS SENSOR ARCHITECTURE WITH A HIGH SENSITIVITY AT LOW TEMPERATURES (71) Applicant: INTERNATIONAL BUSINESS MACHINES CORPORATION, Armonk, NY (US)

(72) Inventors: S. J. Chey, Mount Kisco, NY (US); Hendrik F. Hamann, Yorktown Heights, NY (US); Levente Klein, Tuckahoe, NY (US); Siyuan Lu, Yorktown Heights, NY (US); Roland Nagy, Osterhofen (DE)

(73) Assignee: International Business Machines Corporation, Armonk, NY (US)

( * ) Notice: Subject to any disclaimer, the term of this patent is extended or adjusted under 35 U.S.C. 154(b) by 509 days.

(21) Appl. No.: 15/287,654

(22) Filed: Oct. 6, 2016

(65) Prior Publication Data
US 2017/0023520 A1 Jan. 26, 2017

Related U.S. Application Data (62) Division of application No. 14/798,099, filed on Jul. 13, 2015.

(51) Int. Cl.
G01N 7/00 (2006.01)
G01N 21/00 (2006.01)
(Continued)

(52) U.S. Cl.
CPC ....... G01N 27/4141 (2013.01); C23C 14/086 (2013.01); C23C 14/14 (2013.01);
(Continued)

(58) Field of Classification Search
CPC ............. G01N 27/4141; G01N 27/123; G01N 27/125; G01N 33/0027; G01N 33/0006;
(Continued)

(56) References Cited

U.S. PATENT DOCUMENTS 4,700,716 A * 10/1987 Kasevich ............... A61B 18/18
219/748
4,731,226 A 3/1988 Takahata et al.
(Continued)

FOREIGN PATENT DOCUMENTS

EP 0313390 4/1991
GB 2362959 A 5/2001
(Continued)

OTHER PUBLICATIONS

List of IBM Patents or Patent Applications Treated as Related dated Oct. 6, 2016, 2 pages.
(Continued)

Primary Examiner — Brian J. Sines
(74) Attorney, Agent, or Firm — Tutunjian & Bitetto, P.C.; Vazken Alexanian (57) ABSTRACT A gas sensing device includes a dielectric substrate, a heater integrated into a first side of the substrate and an insulating dielectric formed over the heater. A gas sensing layer is formed on a second side of the substrate opposite the first side. Contacts are formed on the gas sensing substrate. A noble material is formed on a portion of the gas sensing layer between the contacts to act as an ionizing catalyst such that, upon heating to a temperature, adsorption of a specific gas changes electronic properties of the gas sensing layer to permit detection of the gas.

16 Claims, 5 Drawing Sheets (51) Int. Cl.
| | | |
|---|---|---|
| *G01N 27/00* | (2006.01) | |
| *G01N 31/00* | (2006.01) | |
| *G01N 33/00* | (2006.01) | |
| *H01S 4/00* | (2006.01) | |
| *G01N 27/414* | (2006.01) | |
| *G01N 27/12* | (2006.01) | |
| *C23C 14/08* | (2006.01) | |
| *C23C 14/14* | (2006.01) | |
| *C23C 14/30* | (2006.01) | |
| *C23C 14/34* | (2006.01) | |
| *G08B 21/16* | (2006.01) | |
| *G08B 29/18* | (2006.01) | |
| *G08B 29/22* | (2006.01) | |

(52) U.S. Cl.
CPC .............. *C23C 14/30* (2013.01); *C23C 14/34* (2013.01); *G01N 27/123* (2013.01); *G01N 27/125* (2013.01); *G01N 33/0027* (2013.01); *G08B 21/16* (2013.01); *G08B 29/185* (2013.01); *G08B 29/22* (2013.01); *G01N 33/0006* (2013.01); *G01N 33/0047* (2013.01)

(58) Field of Classification Search
CPC ...... G01N 33/0047; G01N 7/00; G01N 21/00; G01N 27/00; G01N 31/00; G01N 33/00; C23C 14/086; C23C 14/14; C23C 14/30; G08B 21/16; G08B 29/185; G08B 29/22; H01S 4/00
USPC ................. 422/83, 90, 98; 436/43, 139, 141
See application file for complete search history.

(56) References Cited

U.S. PATENT DOCUMENTS

| | | | | |
|---|---|---|---|---|
| 4,786,476 A * | 11/1988 | Munakata | ............... | G01N 27/12 204/421 |
| 5,250,170 A * | 10/1993 | Yagawara | ............... | G01N 27/12 204/431 |
| 5,635,628 A | 6/1997 | Fleischer et al. | | |
| 5,767,388 A | 6/1998 | Fleischer et al. | | |
| 6,263,723 B1 | 7/2001 | Takao et al. | | |
| 6,562,215 B1 | 5/2003 | Nelson et al. | | |
| 6,746,584 B1 | 6/2004 | Wang et al. | | |
| 7,356,420 B2 * | 4/2008 | Vilanova | ............... | G01N 27/12 702/22 |
| 8,669,131 B1 | 3/2014 | Smith et al. | | |
| 8,691,609 B1 | 4/2014 | Smith et al. | | |
| 9,482,585 B2 | 11/2016 | Singh et al. | | |
| 9,523,651 B2 | 12/2016 | Humbert et al. | | |
| 2002/0037633 A1 * | 3/2002 | Satou | ............... | B81B 7/0038 438/476 |
| 2003/0159497 A1 * | 8/2003 | Warburton | ............... | G01N 7/08 73/23.31 |
| 2004/0060346 A1 * | 4/2004 | Bonne | ............... | G01N 1/24 73/61.44 |
| 2005/0000981 A1 | 1/2005 | Peng et al. | | |
| 2005/0218465 A1 | 10/2005 | Cummins | | |
| 2006/0017650 A1 * | 1/2006 | Allen | ............... | H01Q 9/0407 343/900 |
| 2006/0063523 A1 | 3/2006 | Norman | | |
| 2006/0202590 A1 * | 9/2006 | Liu | ............... | G01F 1/6882 310/338 |
| 2008/0156074 A1 | 5/2008 | Tobias | | |
| 2008/0282765 A1 | 11/2008 | Bonne et al. | | |
| 2009/0159447 A1 * | 6/2009 | Cui | ............... | G01N 27/125 204/431 |
| 2009/0308747 A1 | 12/2009 | Cramer et al. | | |
| 2009/0324449 A1 | 12/2009 | Kira | | |
| 2010/0065775 A1 * | 3/2010 | Zitoun | ............... | H01M 4/381 252/182.1 |
| 2011/0072879 A1 | 3/2011 | Bellis et al. | | |
| 2011/0118705 A1 * | 5/2011 | Dekker | ............... | G01F 1/6847 604/890.1 |
| 2011/0192718 A1 | 8/2011 | Chou et al. | | |
| 2011/0197657 A1 | 8/2011 | Gole | | |
| 2011/0226041 A1 | 9/2011 | Cummins | | |
| 2013/0285682 A1 | 10/2013 | Biskupski et al. | | |
| 2014/0090834 A1 * | 4/2014 | Sultenfuss | ............ | E21B 43/243 166/248 |
| 2014/0105790 A1 | 4/2014 | Gaudon et al. | | |
| 2014/0175287 A1 * | 6/2014 | Vaillancourt | ... | H01L 31/035218 250/338.4 |
| 2014/0373600 A1 * | 12/2014 | Gole | ............... | G01N 27/128 73/31.06 |
| 2018/0134559 A1 * | 5/2018 | Kuttiyiel | ............. | C01B 21/0622 |

FOREIGN PATENT DOCUMENTS

| | | |
|---|---|---|
| JP | S57127839 | 8/1982 |
| JP | S6383652 | 4/1988 |
| JP | H01196556 | 8/1989 |
| JP | H0455747 | 2/1992 |
| JP | 2005017182 | 1/2005 |
| JP | 2005017242 | 1/2005 |
| WO | 2005119248 A1 | 12/2005 |
| WO | 2008105973 A2 | 9/2008 |

OTHER PUBLICATIONS

List of IBM Patents or Patent Applications Treated as Related dated Feb. 23, 2017, 2 pages.
Basu, S., et al., "NanocrystallineMetal Oxides forMethane Sensors: Role of NobleMetals," Journal of Sensors, vol. 2009, Jul. 2009. (pp. 1-21).
Quaranta, F., "A novel gas sensor based on SnO rOs thin film for the detection of 2 methane at low temperature," Sensors and Actuators B: Chemical, vol. 58, Sep. 1999. (pp. 1-6).
Yingshuo, Y., "Microstructure Methane Sensor Based on Pd-doped Sn02 Nanoparticies," International Conference on Measurement, Information and Control (MIC), May 2012. (pp. 1-4).
U.S. Office Action Issued in U.S. Appl. No. 15/287,632 dated Jun. 28, 2018, 11 pages.
U.S. Office Action issued in U.S. Appl. No. 15/287,632 dated Oct. 5, 2018, 12 pages.

* cited by examiner

RECONFIGURABLE GAS SENSOR ARCHITECTURE WITH A HIGH SENSITIVITY AT LOW TEMPERATURES

BACKGROUND

Technical Field

The present invention relates to gas sensors, and more particularly to a portable $SnO_2$/noble metal gas sensor architecture with an integrated heater for detecting hydrocarbons, such as, methane gas.

Description of the Related Art

Oxide based gas sensors are widely employed in many different industries, e.g., coal mines, fuel production, building intake air quality control, oil and gas (to measure and manage fugitive gases), etc. Commercial oxide based sensors have large power consumption due to the elevated temperature required by the sensor element to achieve high sensitivity and selectivity. State of the art commercial gas sensors work at temperatures between 400 degrees C. and 550 degrees C. The high temperature requirement causes large power consumption that needs to be supplied to a heater element.

Selectivity of the sensor toward different gases is difficult to implement, and factory based calibration may not hold in environments where multiple gases are mixed in the air. On-board calibrating solutions for the sensor can overcome erroneous reading or false alarms in the field.

SUMMARY

A gas sensing device includes a dielectric substrate, a heater integrated into a first side of the substrate and an insulating dielectric formed over the heater. A gas sensing layer is formed on a second side of the substrate opposite the first side. Contacts are formed on the gas sensing substrate. A noble material is formed on a portion of the gas sensing layer between the contacts to act as an ionizing catalyst such that, upon heating to a temperature, adsorption of a specific gas changes electronic properties of the gas sensing layer to permit detection of the gas.

Another sensing system includes a substrate and at least one gas sensing device mounted on the substrate and including a heater integrated therein, a gas sensing layer formed between contacts formed on the gas sensing layer and a noble material formed on a portion of the gas sensing layer between the contacts. A gas canister for storing a known gas is coupled to the substrate, and an injector is configured to release gas from the canister in accordance with a calibration signal such that the at least one gas sensing device is calibrated using locally released gas from the canister.

A method for fabricating a gas sensing device includes forming a heater on a first side of a dielectric layer; depositing an insulating dielectric over the heater; forming a metal-oxide semiconductor gas sensing layer a second side of the dielectric layer opposite the first side; patterning contacts on the gas sensing substrate and depositing a noble material on a portion of the gas sensing layer between the contacts to act as an ionizing catalyst such that, upon heating to a temperature, adsorption of a specific gas changes electronic properties of the gas sensing layer to permit detection of the gas.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

In accordance with the present principles, devices for detecting ambient gases are provided. In one embodiment, to increase efficiency, the device provides a structure for reducing heater element temperature. The structure operates at a low power consumption range while the selectivity and sensitivity maintain operational values. In one embodiment, the structure includes a metal-oxide-insulator structure with a top active gas sensing element exposed to an environment or to the atmosphere. Gas molecules absorbed on an active substrate dissociate creating a change in conductance in an active channel that is electrically measured.

Underneath the structure, a heater is integrated. The heater may include a patterned metal film that can heat up to about 700 degrees C., and the temperature of the top active gas sensing element is adjusted to increase sensor response specificity. Larger operating temperatures are associated with higher power consumption, and for portable applications of the sensor powered by battery, the reduction in energy consumption is highly desirable. The gas sensing structure can operate at a temperature as low as between about 150 degrees C. and 250 degrees C. with a fast sensor response and a short recovery time when subjected to, e.g., methane exposure. Conventionally, low operating temperatures are associated with drifting of the sensor response, which made quantitative measurements difficult, where the signal is compared to a baseline.

In one embodiment, a sensor, in accordance with the present principles, includes a self-calibration feature where a known concentration of gas, e.g., $CH_4$, is released and the sensor reading is updated in a look-up table. Periodic calibration of the sensor will ensure a reliable measurement over an extended period of time.

In a particularly useful embodiment, an $SnO_2$ layer is employed for the detection of gas molecules in the air that can have a thin metal (preferably a noble metal, e.g., Pd, Co, Pt, Ag, etc.) coating on the top, or the coating may include nanoparticles dispersed or self-assembled on the surface to act as a catalyst and increase specificity. The metal catalyst makes the detection specificity of the sensor significant and permits the sensor to distinguish between different chemical species. Differential measurements of multiple sensors that have catalyst of different metals permit consecutive measurements and can distinguish the different gas species.

It is to be understood that the present invention will be described in terms of a given illustrative architecture; however, other architectures, structures, substrate materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

A design for an integrated circuit chip may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 1:
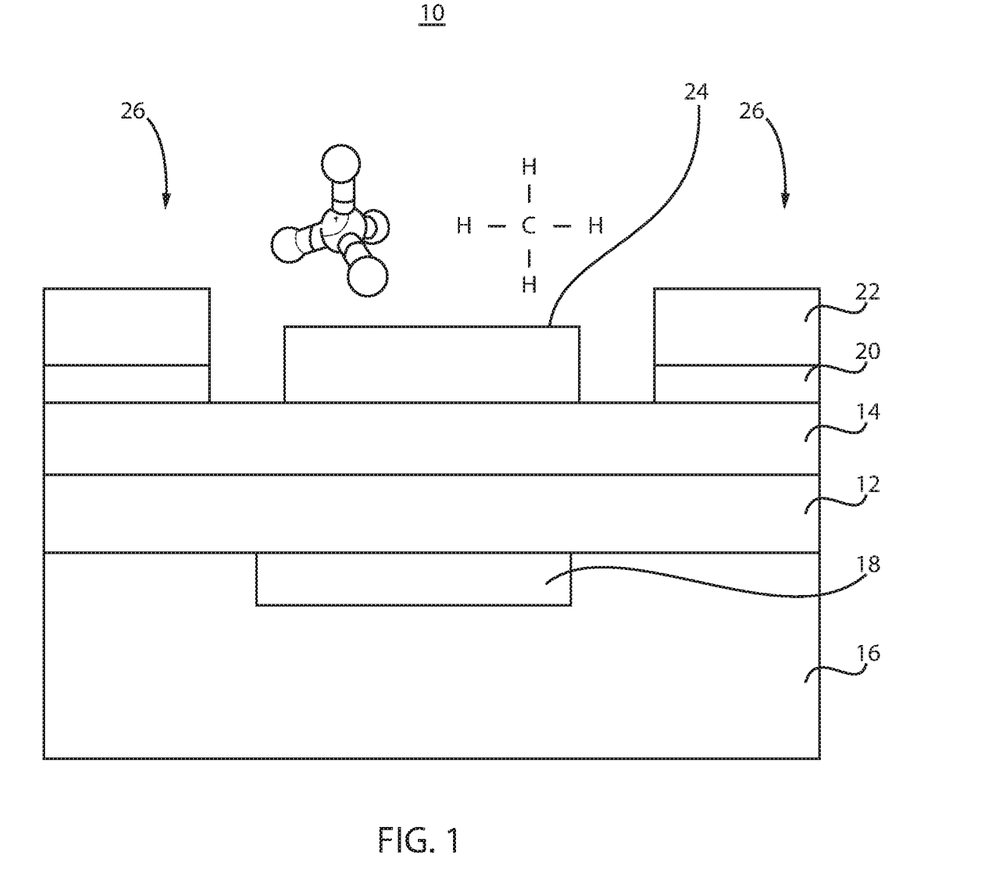
FIG. 1 is a cross-sectional view of a gas sensor with an integrated heater in accordance with the present principles.

Referring now to the drawings in which like numerals represent the same or similar elements and initially to FIG. 1, an illustrative sensor device 10 is shown in cross-section in accordance with the present principles. The device 10 is formed on an insulating substrate 16. The insulating substrate 16 provides thermal insulation to prevent heat loss from an integrated nanoheater or heating element 18. The insulating substrate 16 may include a ceramic material, glass or other material capable of handling operational temperatures of the sensor device 10.

In one embodiment, a three layer architecture is employed. A dielectric layer 12 is formed over the nanoheater 18 and the insulating substrate 16. The dielectric layer 12 may include $SiO_2$ or other dielectric material and prevent current leakage from the heater element to the gas sensing layer. The dielectric layer 12 may include a thickness of about 200 nm, although other thicknesses are also contemplated. A gas sensing substrate 14 is formed over the dielectric layer 12. The gas sensing substrate 14 may include a $SnO_2$ layer of about 100 nm in thickness, although other thicknesses may be employed. On the top of the gas sensing substrate 14, a metal layer 24 is deposited that facilitates gas adsorption. The metal layer 24 preferably includes an inert or noble metal, such as Au, Ag, Pd, Pt, Rh, Co, or the like. One particularly useful metal includes Pd, which is sensitive for methane detection. The metal layer 24 may include a thickness of about 3 nm, although other thicknesses may be employed. The metal layer 24 can be broken up into a nanoparticle layer by thermally annealing the structure after being formed.

Contacts 26 are formed and patterned on the gas sensing substrate 14. The contacts 26 may include a bilayer structure comprised of an interface layer 20 and a contact layer 22. In one embodiment, the interface layer 20 may include Ni and may be about 100 nm in thickness, although other materials and thicknesses may be employed. The contact layer 22 may include Al and is about 100 nm in thickness, although other materials and thicknesses may be employed.

The nanoheater 18 can tune the temperature of the gas sensing substrate 14 (e.g., $SnO_2$ layer). In many situations, when the nanoheater 18 generates heat, the heat could be absorbed by the underlying insulating substrate 16 making uniform heating of the top surface difficult. In general, the heat emission is highly localized above the heater substrate forcing the heater to be similar in size to the gas sensing layer to ensure uniform temperature for the sensing element.

In accordance with one aspect of the present principles, the heat distribution is improved by using an antenna structure (e.g., Yagi Uda antenna structures) to extend the area where the heat is spread. A Yagi Uda antenna may be coupled to the heater 18 to provide efficient coupling of the infrared radiation (heat) to the gas sensing substrate 14, minimizing the heat absorption by the insulating substrate 16. The nanoheater 18 may be sized to reduce power consumption, e.g., width should be reduced while increasing its length, to focus heat energy. To overcome inefficient heat transfer between the heating element 18 and the gas sensing layer 14, the heater width is tuned to change the directional emission of the nanoheater 18 utilizing plasmonic resonances. For example, to avoid heat from being absorbed by the underlying insulating substrate 16, the nanoheater 18 is structured to direct heat upwards using the antenna structures. Therefore, to reduce power consumption, the nanoheater 18 width can be reduced while increasing its length (into the page of FIG. 1) to provide a more uniform heating distribution for the gas sensing layer 14. The antenna elements will amplify the heat distribution, and their placement and operation will increase heat transfer efficiency.

Figure 2:
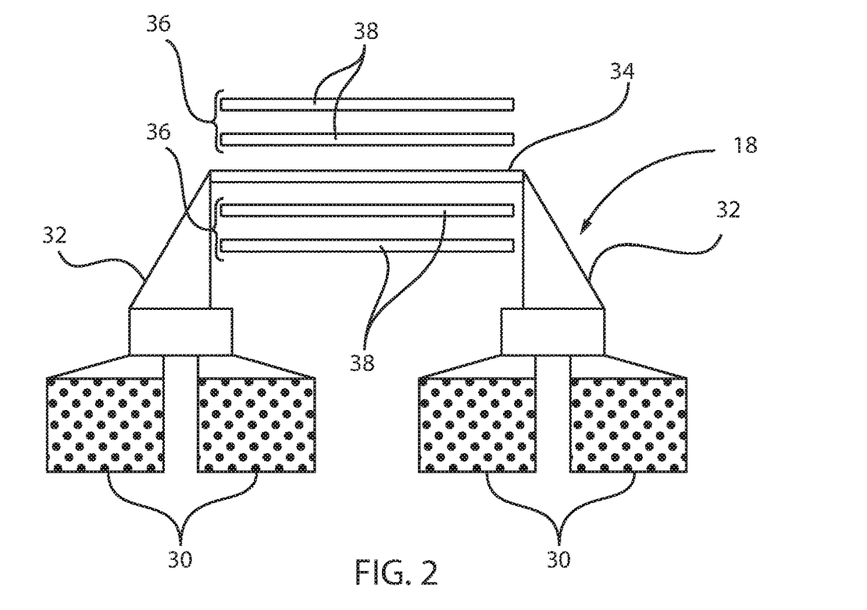
FIG. 2 is a schematic diagram showing a heater with Yagi Uda antenna elements integrated therein in accordance with the present principles.

Referring to FIG. 2, a top perspective view shows the nanoheater 18 relative to Yagi-Uda antenna elements 38. The nanoheater 18 may be configured in a plurality of ways. In one embodiment, the nanoheater 18 includes an electrical element 34 (e.g., a resistor) in which current is passed to generate heat. The electrical element 34 connects to electrical contacts 30 (coming out of the page) using conductors 32. In accordance with the present principles, a more uniform heat distribution can be achieved using an infrared Yagi Uda based antenna 36 that tunes the infrared radiation emission based on periodic spaced elements 38. The elements 38 may include Pt or other metals.

Figure 3A:
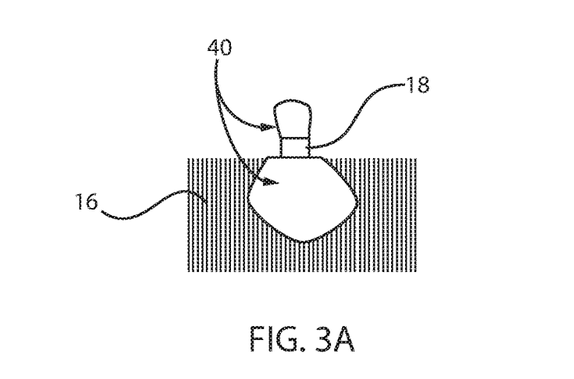
FIG. 3A is a diagram showing a heat distribution without Yagi Uda antenna elements.
Figure 3B:
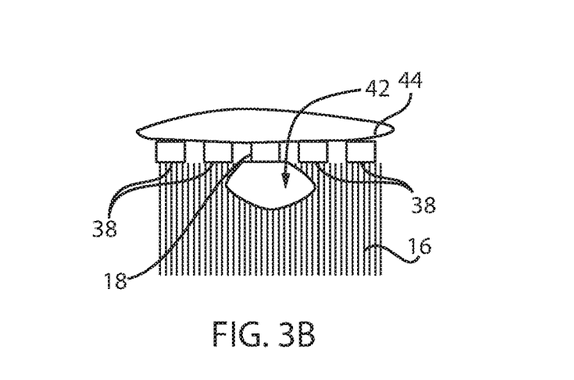
FIG. 3B is a diagram showing a heat distribution with Yagi Uda antenna elements in accordance with one embodiment.

In FIG. 3A, an illustrative heat distribution pattern 40 is shown for a nanoheater 18 employed without the Yagi Uda based antenna. In FIG. 3B, an illustrative heat distribution pattern 42 is shown for a nanoheater 18 employed with the Yagi Uda based antenna elements 38. An upper heat emission pattern 44 is more evenly distributed over the device as shown in FIG. 3B.

Referring again to FIG. 2, the distance between heater 18 and Yagi Uda antenna elements 38 and also the size of the Yagi Uda elements 38 can be employed to tune an emission wavelength of the heaters 18 and be tuned toward a wavelength where methane gas absorbs light. For example, a heater size could be about 500 nm wide and have a length of about 2 microns while the spacing between the antenna elements 38 could be between about 2 and 3 microns. The spacings can be tuned such that wavelengths are sensitive to different gases and adjusted for different gases, e.g., methane ($CH_4$), $CO_2$, CO, etc.

Referring again to FIG. 1, during operation, the sensor device 10 can be exposed to air. Different gases like methane can be adsorbed at the surface of the gas sensing substrate 14 (e.g., $SnO_2$) and react with electrons which produce ionized gas. The ionized gas (e.g., oxygen, etc.) is responsible for a band bending shift that creates a depletion layer around the grain boundaries of the gas sensing substrate 14 (e.g., $SnO_2$). Gas molecules to be sensed in the air will be adsorbed to the surface and react with the ionized oxygen or other gas. This reaction causes a change in the depletion layer which reduces the conductivity of the gas sensing substrate 14 (e.g., $SnO_2$).

In one embodiment, the sensor device 10 includes a metal-oxide semiconductor gas sensor with the heater 18 modified to be a Yagi Uda antenna for the detection of methane gas. The Yagi Uda antenna elements are positioned at a distance that enhances emission, e.g., around 3.4 microns (the methane absorption wavelength). The antenna elements 38 are configured to have an aspect ratio larger than twenty and dimensions larger than the emission wavelength. The sensor device 10 is operated at about 150-250 degrees C. (using the heater 18) with a high discrimination of $CH_4$ against $CO_2$ and CO.

The gas sensing substrate 14 includes an ultrathin $SnO_2$ sensing layer with a thin metal (e.g., Pd, Pt, Rh, etc.) layer 24 that may be broken up into nano-particles through thermal annealing. The break-up of the metal film 24 into particles will increase surface area and the probability of absorbing $CH_4$ molecules. A lower detection limit is also increased in this way. The sensitivity is further enhanced by controlling the size of $SnO_2$ grains of the substrate 14 that are deposited. In one particularly useful embodiment, particle size may be about 100 Angstroms or less in diameter.

Figure 4:
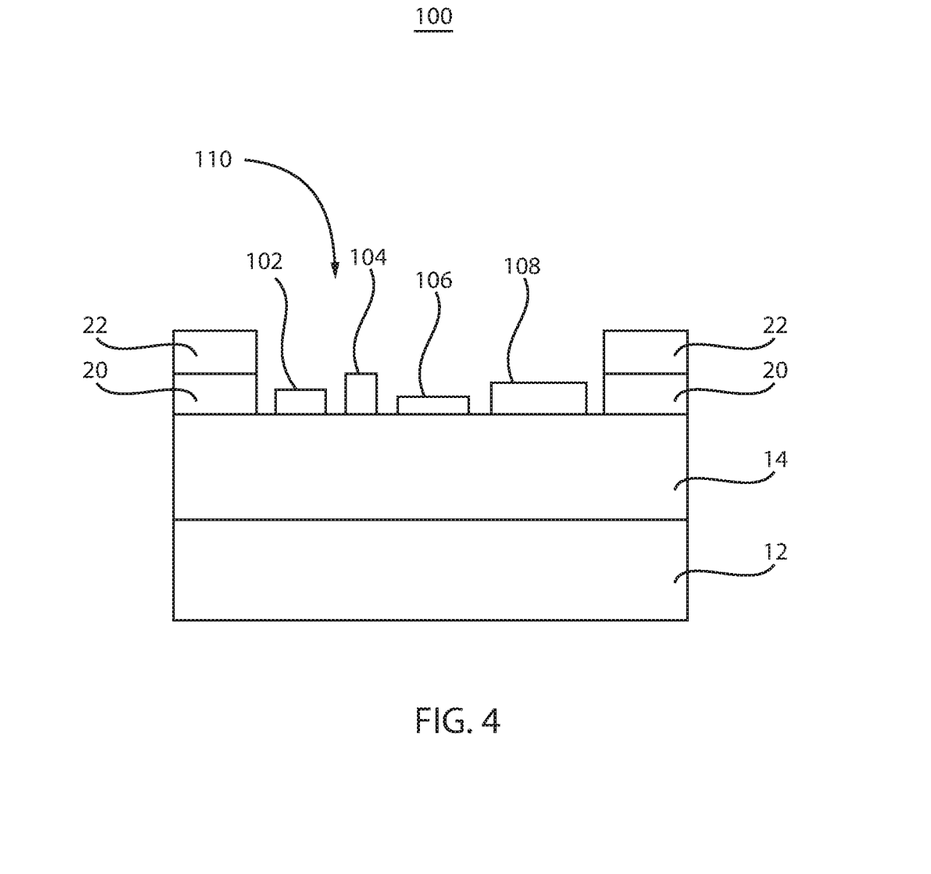
FIG. 4 is a cross-sectional view of a gas sensor having multiple noble material structures thereon for sensing different gases at different temperatures in accordance with the present principles.

Referring to FIG. 4, another embodiment shows a sensor device 100 having a metal film 110 forming a plurality of different catalyst materials (102-108) on the gas sensing substrate 14. The device 100 may include thin metals for catalyst materials 102-108, e.g., catalyst 102 may include Pd, catalyst 104 may include Pt, catalyst 106 may include Rh, catalyst 108 may include Pt—Ag, etc. There may be one or more catalysts, and the catalysts may include pure metals, metal alloys, combinations of metals, etc. The sensitivity of the device 100 may be configured by using different combinations and geometries of noble materials as the catalysts on the sensor surface. The thickness and the surface to volume ratio of the noble materials of the film 110 is responsible for the sensitivity of the sensor 100. For example, using a thin layer of, e.g., Pd (3 nm) as a surface catalyst the sensor 100 shows a high sensitivity specifically to methane, etc.

The metal film 110 can be patterned such that the surface to volume ratio is increased. In one example, a nanoporous membrane is created from the film 110 based on anodic reduction. Alternatively, nanoparticles can be deposited on the surface, or the film 110 can be patterned using e-beam lithography. With different sizes and thicknesses of noble materials, the sensitivity, at low operational temperatures, can be adjusted for different gases.

To calibrate the system, a set of measurements are performed where the sensor response to different gas concentration is established:

$$\frac{\Delta R}{R_0} = (CH_4)^a (CO_2)^b \exp\left(\frac{E_a}{k_B T}\right) \exp(c \cdot RH), \quad \text{(Eq. 1)}$$

where $\Delta R$ is the change in resistance as methane gas is absorbed in the surface; Ro is reference resistance of the sensor with no methane gas in the air, $k_B$ is the Boltzmann constant, T is absolute temperature, RH is relative humidity, a is scaling factor, b is scaling parameter, c is a scaling parameter, $E_a$ is the activation energy, ($CH_4$) and ($CO_2$) are concentrations of the respective gases. The values for a, b, c, $E_a$ are determined for all different materials by fitting change in resistance to changes caused by the well-known gas exposures. Each catalyst (e.g., Pd. Pt, Rh, etc.) and sensor geometry will have a set of parameters (a, b, c, $E_a$). The sensor 100 will be characterized with respect to principal components analysis where the discrimination of different sensor geometry and catalyst particles to different gases is quantified. A set of measurements may be based on parameters, and a determination of a best fit of the sensor response to all possible combinations of parameters.

Device 100 may be employed to detect different gases under different conditions. For example, a set of parameters may be adjusted to detect a first gas, then another set of parameters are adjusted to detect a second gas and so on. In one example, a gas may be sensitive to a particular noble material and a temperature. Another gas may be sensitive to the same noble material at a different temperature, and so on.

When multiple sensors are deployed at the same time where each sensor can have a specific catalyst layer (102-108) and is initially calibrated or tuned to be sensitive to a specific gas either by heater design (pitch of antenna elements), catalyst particle types or operating temperatures. An atmospheric composition may be reconstructed from a multi-sensor measurement where each sensor will measure one or two components of the environmental gases at the same time. In one embodiment, multiple sensors (on a same device or on different device working together) may have calibrated responses to different gases where different catalyst particles on the surface will have a specific response to different gases. The sensor may have a different discriminated sensor response to each different gas. In one embodiment, a first sensor temperature may be employed to measure a first gas concentration and then changed to a second temperature to measure for a second gas. Each gas may react with a same catalyst or a different catalyst on the gas sensing layer.

In accordance with the present principles, gas sensing devices 10, 100, include open transistor architectures including a fine grain sensing substrate 14 (e.g., 100 Angstrom grain structure) for a $SnO_2$ film with nano-particles (thin metal film 24, 110 formed thereon. The device can be operated at temperatures as low as 150 degrees C. with sub ppm sensitivity toward methane. The nano-particles of the metal film 24, 110 can be tuned by material choice, geometry, etc. to be specific to detection of particular gases. In useful embodiments, multiple sensors may be operated simultaneously to distinguish between multiple gases that may be present (e.g., $CH_4$, $H_2S$, $SO_2$, etc.). The sensors 10, 100 may include an integrated Yagi Uda antenna that is tuned to emit infrared radiation (e.g., at 3.4 microns for methane) by positioning the metal antenna elements around the nanoheater 18. The size of the sensor is preferably narrower than the Yagi Uda antenna such that uniform heating is provided. The sensor device or devices may be part of a larger system. The system may include multiple sensors and may include a nearby integrated gas calibration module that permits periodic recalibration of the sensor or sensors. The sensor or sensors may be integrated with a wireless sensor network where each sensing node may include a microprocessor and a radio.

Figure 5:
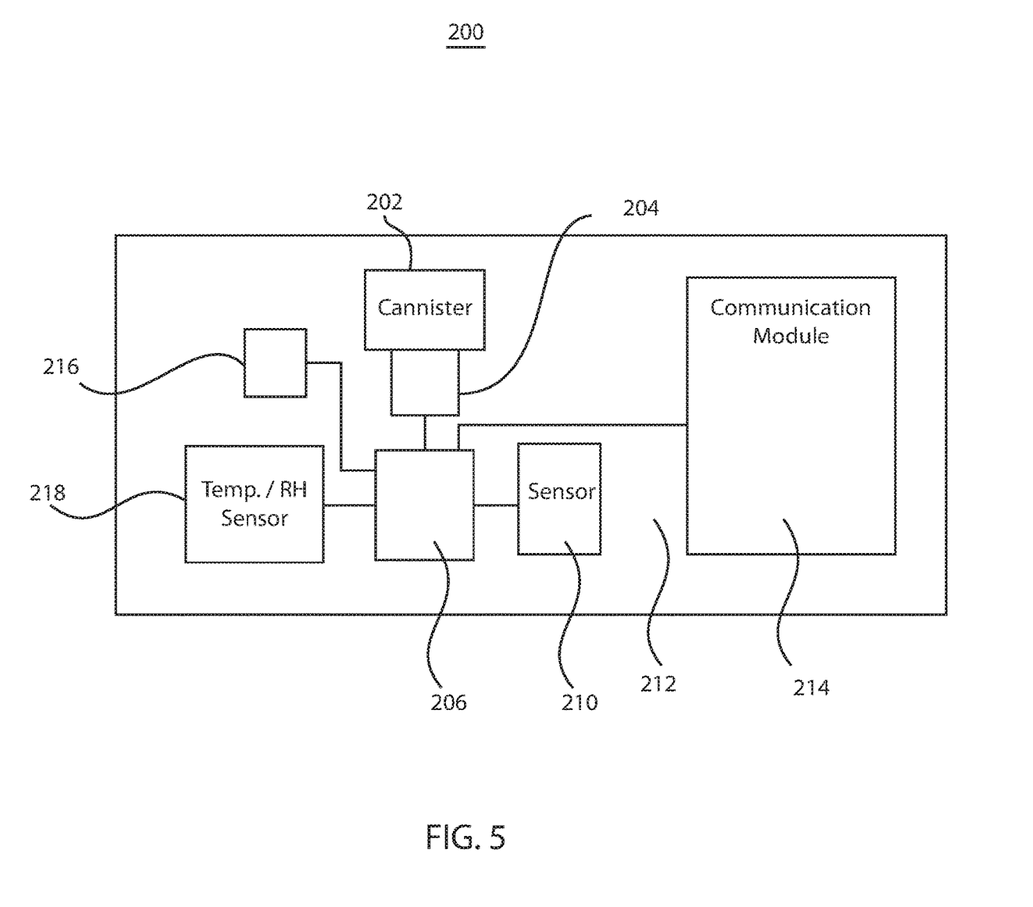
FIG. 5 is a schematic diagram showing a system including a built-in calibration feature, and communication module to communicate measurements in accordance with the present principles.

Referring to FIG. 5, a schematic block/flow diagram shows a sensor system 200 in accordance with one embodiment. The sensor system 200 may be implemented on a substrate 212, such as a silicon substrate as an integrated circuit or a printed wiring board. The sensor system 200 includes a sensor device 10, e.g., a volatile organic compound (VOC) sensor. The sensor system 200 includes a self-calibration capability built-in, where a calibration gas included in a canister or storage device 202 is employed periodically to evaluate a resistance change in the gas sensing substrate (e.g., $SnO_2$ film) to one or more gases to permit calibration. The calibration gas is provided using an injector or micropump 204, which may include a piezoelectric nanoliter injector similar to an inkjet printhead.

To calibrate the sensor response the container 202 containing a well-known gas concentration is included on the same board 212 where a small amount of gas is released to calibrate the sensor response. The micropump 204 releases the gas, e.g., propane, methane, etc. The sensor reading is updated in memory 216 to provide a reliable reading. Both temperature and relative humidity may be measured by a temperature/humidity sensor(s) 218, which are recorded as a way to assess a shift in sensor readings in response to environmental changes.

The small canister 202 of a surrogate gas is released through controlling a piezoelectric controlled nanoliter injector 204 to release a controlled amount of gas to calibrate the VOC sensor 210. A 0.5 ml canister will last the life-time of the device. More than one canister may be employed. The multiple canisters may include a same or different gases.

A controller or processor 206 (e.g., a microprocessor) may initiate a calibration method which intermittently activates the injector 204 to release the calibration gas to calibrate the sensor 210. The sensor 210 may be designed as an array of sensors where the catalyst can be Pd, Pt, Rh, etc., and each of the metals has an increased sensitivity toward a set of gases at a given temperature. The gases may be sensitive to different combinations of catalysts and temperatures. The array can discriminate between different gases, e.g., $CH_4$, $H_2S$, $CO_2$, CO, etc. Sensors 210 can be connected in series or in parallel for single or pulsed operation.

Sensor 210 can be operated in a continuous powered mode or in a transient mode where a small heating pulse is applied, and the system 200 will start to warm up but the measurement will be taken before the sensor 210 reaches its equilibrium temperature. Pulsed operation can significantly reduce the power consumption of the sensor element. The microprocessor 206 can provide a pulse sequence that provides for transient heating of the sensor 210. When all sensors are operating in pulsed mode a same voltage pulse can power all sensors and measure their transient response to extract multi-component gases. The sensor 210 or sensors are operated in a pulsed mode to minimize power consumption.

Low power consumption opens the possibility to apply the sensor 210 in portable devices or as part of a wireless sensor network where the sensor will be triggered to acquire one measurement once an event is signaled. The system 200 may include a communications module 214 (e.g., a radio) to communicate with the wireless sensor network or any suitable network.

A distributed sensing system (not shown) using sensors 201 or system 200 has applications in oil and gas industry, environmental tracking, and other gas monitoring applications, e.g., applications where multiple sensor readings are fused (over the Internet) with physical models to assess contamination levels, etc. In one example, a gas fracking operation may need to monitor methane gas leaks to be documented on a periodical basis. Similar applications are in livestock monitoring to quantify methane gas generation.

One particularly useful application includes employing the sensing system in the gas extraction industry to ensure compliance and open the possibility to manage sensing data in a data store, provide analytics using analytics servers and cloud solutions to companies. This would assist in ensuring compliance with Environmental Protection Agency (EPA) regulations and ensure employee safety around extraction points.

One or more $CH_4$ sensors, in accordance with the present principles, may be deployed nearby a gas extraction well where $CH_4$ escape is monitored in real-time. Each sensor may be battery operated or otherwise powered and be part of a multimodal distributed sensor network (e.g., a mesh network). The network may include other sensors and equipment, e.g., optical sensors, anemometers, a remote gateway and cellular modems for communications, etc. The sensors may be connected to or be integrated with a microprocessor and a radio, and sensor information may be transmitted wirelessly and collected across a large area using links to one or more different networks. Such networks may include a satellite communications, a cellular communications, wide area network communications, local area networks communications, etc.

Network computers may be employed to store, process and distribute data as needed. For example, data may be sent to clients, a data store, analytics computers, uploaded to links (for other networks), etc. The data may be combined with other information to provide additional context. For example, weather data, e.g., from a satellite, may be combined or reported with the analytics or with the raw data readings to provide comparison context or a better understanding of the readings. For example, an anemometer or wind sensor can indicate the direction of flow. A sensor in the path of wind flow will sample more often. Once a threshold is reached, the sensor could send a command to a central computer that would wake up all other sensors. The central computer can continuously assign a sensor the task to sniff the air. The sensor may be in the direction of the wind. If a threshold level is reached, the sensor will send a message to the central computer that will provide a schedule to localize leak and concentration level at the leak. The sensor(s) provide low power operation and employ a low operating temperature. At a temperature of about 150 degrees C. a sensitivity of less than 50% for 10 ppm methane can be achieved. The sensor can detect methane in the ppb range.

Multiple measurements may be taken that are fed into a dispersion model stored on a computer to localize leaks and assess the leak size and flow rate for the gas escape. Data may be combined with observation from a satellite to distinguish if the leak has no natural causes, like coming from a swamp or agricultural locations to eliminate false alarms. An alarm may be sent out if the leak level is above the regulation set level.

Figure 6:
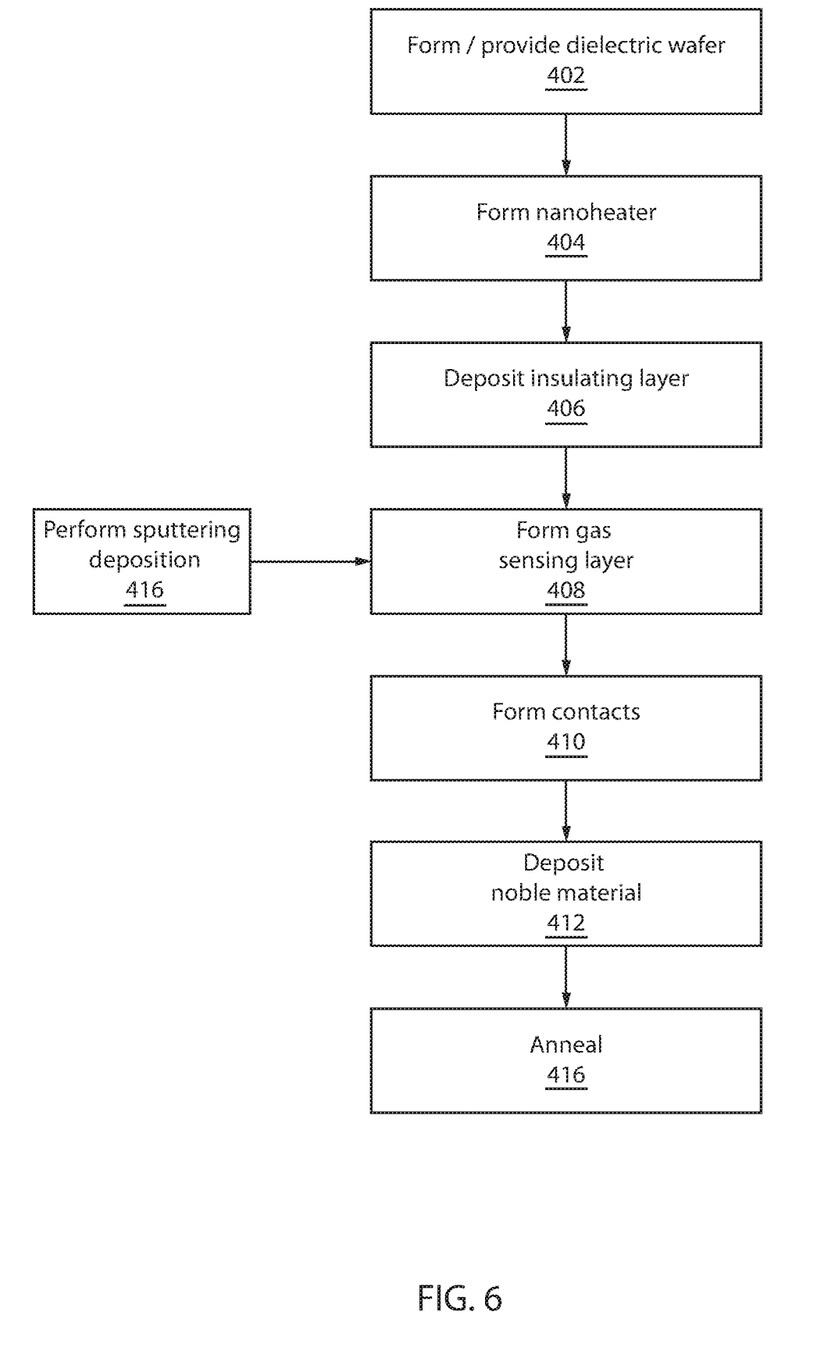
FIG. 6 is a block/flow diagram showing a fabrication method for fabricating a gas sensor in accordance with one illustrative embodiment.

Referring to FIG. 6, in accordance with the present principles, gas sensors are provided in transistor form. The transistors have adjustable sensitivity/selectivity and operate at low temperatures (e.g., 150 degrees C.) using a thin film $SnO_2$ semiconductor gas sensor with low power consumption. Thin film architecture includes noble metal catalyst materials and an integrated nanoheater for reduced power consumption based on tunable emission wavelength that would enhance the selectivity of gas absorption on the catalyst. An illustrative method is described in forming the gas sensors in accordance with the present principles.

In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In block 402, a dielectric wafer is provided or formed, which may include $SiO_2$ layer on the top of a thickness of about 200 nm. In block 404, a nanoheater is formed on the wafer. The nanoheater may be formed using a metal, such as Pt, although other material may be employed. The nanoheater may include a Yagi Uda antenna formed on the wafer. In block 406, an insulating layer is deposited over the nanoheater. The insulating layer may include a 100 nm $SiO_2$ layer formed using e.g., chemical vapor deposition (CVD).

In block 408, a gas sensing layer is formed. The gas sensing layer may include a 100 nm $SnO_2$ layer formed on the wafer opposite the nanoheater. In an example of block 416, the gas sensing layer may be formed by a deposition process using an RF Magnetron Sputtering process set to a power of 125 W, a 99.99% $SnO_2$ target, a Ar process gas pressure of 6.5 mTorr and a base chamber vacuum of $1\times10^{-7}$ Torr. The chamber may be pumped using, e.g., a Turbo molecular pump. The time for a deposition of the 100 nm $SnO_2$ with at a rate of 0.57 \AA/sec at room temperature was 1740 s. The sheet resistance of the 100 nm $SnO_2$ sample was about 2500 Ohms/Square.

In block 410, contacts are formed. To improve adhesion and form contacts, 100 nm Ni may be employed, followed by 100 nm Al as contact metals. The contacts can be formed using a metal mask and E-beam evaporation. The contacts are improved if a 100 nm thickness of Ni and Al are employed on the $SnO_2$ layer. In block 412, noble materials (metals) are deposited and patterned on top of the gas sensing layer ($SnO_2$) with E-beam evaporation and a metal mask. In one example, the noble materials include Pd, Pt, Rh, Ag, Au, combinations of metals (Pt—Ag), etc.

In one embodiment, a slug with 99.99% purity of Pd may be employed with the E-beam evaporation process. A base chamber vacuum of $1\times10^{-7}$ Torr was employed to minimize contamination from other metals and improve adhesion of metal layer. The deposition rate of 0.1 nm/s was performed to achieve a 3 nm metal layer of Pd and ensure continuous film growth. Other metals and geometries may also be provided.

In block 416, the noble metals can be processed to increase surface area and improve gas sensitivity. In one embodiment, this is achieved by thermal annealing to break up the layer into nanoparticles.

Having described preferred embodiments for reconfigurable gas sensor architecture with a high sensitivity at low temperatures (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A method for fabricating a gas sensing device, comprising:
   forming a heater in an insulating substrate, the heater including an array of a plurality of antenna elements each being spaced apart at a distance corresponding to an absorption wavelength of a gas to be detected and configured to distribute thermal energy when in operation;
   depositing a dielectric layer over the heater;

forming a metal-oxide semiconductor gas sensing layer on the dielectric layer;

patterning contacts on the metal-oxide semiconductor gas sensing layer; and depositing a noble material on a portion of the gas sensing layer between the contacts to act as an ionizing catalyst such that, upon heating to a temperature, adsorption of a specific gas changes electronic properties of the metal-oxide semiconductor gas sensing layer to permit detection of the gas.

2. The method as recited in claim 1, wherein the array of antenna elements includes a plurality of Yagi Uda antenna elements configured to distribute heat to the metal-oxide semiconductor gas sensing layer in a uniform manner, and further comprising heating the metal-oxide semiconductor gas sensing layer with the heater to a temperature between about 150 to about 250 degrees C.

3. The method as recited in claim 1, wherein sensitivity to a gas to be detected is increased by at least one of:

forming grain boundaries in the metal-oxide semiconductor gas sensing layer of a particular size; and selecting a material and geometry for the noble material to be sensitive to detection of different gases at different temperatures.

4. The method as recited in claim 1, wherein the heater is formed to have a width and a length to provide a substantially uniform heating distribution for the metal-oxide semiconductor gas sensing layer in order to reduce power consumption and to focus heat energy.

5. The method as recited in claim 1, wherein the metal-oxide semiconductor gas sensing layer sensitivity is controlled by the size of grains of the metal-oxide semiconductor gas sensing layer.

6. The method as recited in claim 1, wherein the forming the metal-oxide semiconductor gas sensing layer includes sputtering a $SnO_2$ target in an Ar gas chamber.

7. The method as recited in claim 1, wherein the patterning the contacts includes using a metal mask and electron-beam evaporation.

8. The method as recited in claim 1, wherein sensitivity to the gas to be detected is increased by thermal annealing the noble material to break up the noble material into nanoparticles.

9. A method for fabricating a gas sensing device to detect a gas including a hydrocarbon, comprising:

forming a heater in a trench disposed within an upper surface of an insulating substrate, the heater including a plurality of Yagi Uda antenna elements each spaced apart at a distance corresponding to an absorption wavelength of a gas to be detected and configured to distribute thermal energy when in operation;

depositing an insulating dielectric layer on top of the heater and the insulating substrate;

forming a metal-oxide semiconductor gas sensing layer on the insulating dielectric layer;

patterning contacts on the metal-oxide semiconductor gas sensing layer; and depositing a noble conductive material on a portion of the gas sensing layer between the contacts to act as an ionizing catalyst such that, upon heating to a temperature, adsorption of a specific gas changes electronic properties of the metal-oxide semiconductor gas sensing layer to permit detection of the gas.

10. The method as recited in claim 9, wherein the plurality of Yagi Uda antenna elements is configured to distribute heat to the metal-oxide semiconductor gas sensing layer in a uniform manner, and further comprising heating the gas sensing layer with the heater to a temperature between about 150 to about 250 degrees C.

11. The method as recited in claim 9, wherein sensitivity to a gas to be detected is increased by at least one of:

forming grain boundaries in the metal-oxide semiconductor gas sensing layer of a particular size; and selecting a material and geometry for the noble conductive material to be sensitive to detection of different gases at different temperatures.

12. The method as recited in claim 9, wherein a width and a length of the heater are adjusted to reduce power consumption and to focus heat energy.

13. The method as recited in claim 9, wherein the metal-oxide semiconductor gas sensing layer sensitivity is controlled by the size of grains of the metal-oxide semiconductor gas sensing layer.

14. The method as recited in claim 9, wherein the forming the metal-oxide semiconductor gas sensing layer includes sputtering a $SnO_2$ target in an Ar gas chamber.

15. The method as recited in claim 9, wherein the patterning the contacts includes using a metal mask and electron-beam evaporation.

16. The method as recited in claim 9, wherein sensitivity to the gas to be detected is increased by thermal annealing the noble conductive material to break up the noble conductive material into nanoparticles.

\* \* \* \* \*

UNITED STATES PATENT AND TRADEMARK OFFICE
CERTIFICATE OF CORRECTION

PATENT NO. : 10,697,928 B2
APPLICATION NO. : 15/287654
DATED : June 30, 2020
INVENTOR(S) : S. J. Chey et al.

Page 1 of 1

It is certified that error appears in the above-identified patent and that said Letters Patent is hereby corrected as shown below:

On the Title Page

Item (72) Inventors: DELETE "S. J. Chey" and insert --Sukjay Chey--

Signed and Sealed this
Twenty-ninth Day of September, 2020

Andrei Iancu
*Director of the United States Patent and Trademark Office*